(12) United States Patent
Shadduck

(10) Patent No.: US 6,508,816 B2
(45) Date of Patent: Jan. 21, 2003

(54) MEDICAL INSTRUMENT WORKING END CREATING VERY HIGH PRESSURE GRADIENTS

(76) Inventor: John H. Shadduck, 1490 Vistazo West, Tiburon, CA (US) 94920

( * ) Notice: Subject to any disclaimer, the term of this patent is extended or adjusted under 35 U.S.C. 154(b) by 151 days.

(21) Appl. No.: 09/782,649

(22) Filed: Feb. 12, 2001

(65) Prior Publication Data

US 2001/0037106 A1 Nov. 1, 2001

Related U.S. Application Data

(63) Continuation-in-part of application No. 09/181,906, filed on Oct. 28, 1998, now Pat. No. 6,210,404, which is a continuation-in-part of application No. 09/049,711, filed on Mar. 27, 1998, now Pat. No. 6,053,909.
(60) Provisional application No. 60/080,248, filed on Apr. 1, 1998, provisional application No. 60/080,244, filed on Apr. 1, 1998, provisional application No. 60/106,026, filed on Oct. 28, 1998, and provisional application No. 60/106,025, filed on Oct. 28, 1998.

(51) Int. Cl.[7] ............................................. A61B 18/18
(52) U.S. Cl. ............................ 606/34; 606/41; 606/46; 606/50; 607/101
(58) Field of Search .......................... 601/2–3; 606/38, 606/41–50, 159, 32, 34; 607/101

(56) References Cited

U.S. PATENT DOCUMENTS

| 4,682,596 | A | * | 7/1987 | Bales et al. |
| 5,122,138 | A | * | 6/1992 | Manwaring |
| 5,318,014 | A | * | 6/1994 | Carter |
| 5,524,620 | A | * | 6/1996 | Rosenschien |
| 5,669,907 | A | * | 9/1997 | Platt, Jr. et al. |
| 5,695,507 | A | * | 12/1997 | Auth et al. |
| 5,697,281 | A | * | 12/1997 | Eggers et al. |
| 5,700,262 | A | * | 12/1997 | Acosta et al. |
| 5,735,811 | A | * | 4/1998 | Brisken |

OTHER PUBLICATIONS

Topaz, et al., "Acute Results, Complications, and Effect of Lesion Characteristics on Outcome With the Solid–State, Pulsed Wave, Mid–Infrared Laser Angioplasty System," Lasers in Surg. & Med.22:228–239 (1998).*

* cited by examiner

Primary Examiner—Linda C. M. Dvorak
Assistant Examiner—David M. Ruddy
(74) Attorney, Agent, or Firm—Fish & Neave; Nicola A. Pisano

(57) ABSTRACT

A micro-catheter system utilizing a microjoule pulsed electrical discharge between first and second electrodes in a recessed lumen at the catheter working end for creating a cavitating volume of electrolytic fluid composition including a pharmacologic agent. The expansion and collapse of media at a high repetition rate creates acoustic waves that propagate distally from the working end of the micro-catheter to disrupt thrombus. The expansion and collapse of such cavitation bubbles "jet" the pharmacologic agent at a controlled velocity into the acoustically-disrupted thrombus to further depolymerize the thrombus. The catheter system includes a computer-controller for independent modulation of (i) all aspects of pharmacologic agent delivery, and (ii) all parameters of electrical discharge to "tailor" the combined acoustic wave effects and pharmacologic agent effects to dissolve thrombus rapidly and efficiently.

23 Claims, 12 Drawing Sheets

AT TIME = T_ZERO

AT TIME = T$_{+2}$ a.u.

AT TIME = $T_{ZERO}$

AT TIME = T+1 a.u.

AT TIME = T+2 a.u.

MEDICAL INSTRUMENT WORKING END CREATING VERY HIGH PRESSURE GRADIENTS

CROSS-REFERENCE TO RELATED APPLICATIONS

This application is a continuation-in-part of U.S. patent application Ser. No. 09/181,906, filed Oct. 28, 1998, now U.S. Pat. No. 6,210,404 which is related to the following commonly owned regular or provisional United States patent applications, all of which are incorporated herein by this reference: Ser. No. 09/049,711, filed Mar. 27, 1998, now U.S. Pat. No. 6,053,909 titled "Ionothermal Delivery System and Technique for Medical Procedures;" Serial No. 60/080,248, filed Apr. 1, 1998 titled "ionothermal System and Technique for Refractive Procedures;" Serial No. 60/080,244, filed Apr. 1, 1998 titled "Ionothermal System and Technique for Dermal Treatment;" Serial No. 60/106,026, filed Oct. 28, 1998 titled "Micro-Catheter for Combination Acoustic-Pharmacologic Thrombolysis In Stroke Patients;" and Ser. No. 60/106,025, filed Oct. 28, 1998 titled "Micro-Catheter for Electroacoustic and Photoacoustic Thrombolysis In Stroke Patients."

FIELD OF THE INVENTION

The present invention relates to a micro-catheter device utilizing $\mu J$ electrical discharges for the dissolution of thrombus in blood vessels, and more particularly for such treatments in the small diameter circulatory arteries of the brain in victims of stroke. It further relates to a technique for electroacoustic wave propagation against thrombus contemporaneous with high-velocity projection or jetting of pharmacologic agents against thrombus, the combination of acoustic wave or mechanical effects with pharmacologic thrombolysis being adapted to cause rapid dissolution or depolymerization of fibrin in thrombus.

BACKGROUND OF THE INVENTION

In the treatment of thrombus in a blood vessel, either in cardiac patients or stroke victims, conventional treatment is the intravenous administration of pharmacologic agents, such as t-PA (tissue plasminogen activator), streptokinase or urokinase. In such intravenous drug deliveries, the probability of success may be less than about 50 percent, and the success rates are limited by the fact that agents are not delivered directly to the site of the thrombus.

To ablate thrombus in an invasive procedure, various energy-based catheters have been developed, for example utilizing laser and ultrasound energy delivery systems. A disadvantage of such approaches is that the catheter diameter may be too large, and the catheter's flexibility may be limited, thus preventing the working end of the catheter from reaching the thrombus site in the small circulatory arteries of the patient's brain.

Another disadvantage of such catheters is the technique associated with positioning the catheter's working end in close proximity to thrombus prior to energy delivery to have the desired effect. For example, in using a pulsed laser catheter for the ablation or photo-disruption of thrombus, the pioneering technique relied on the steady advance of the working end through the target lesion while continuously emitting pulsed laser energy. The photonic energy of the laser is absorbed by the thrombus if the working end is positioned properly. Investigators found that such laser treatment could cause excessive thermal effects and damage vessel walls.

More recently, the original laser-catheter technique has been modified to a "pulse-and-retreat" approach to reduce thermal effects. In other words, the laser pulses are commenced for a brief "session" just before the working end reaches the target lesion, and then the pulsing is paused for about 60 seconds before advancing the working end for another lasing "session." The pause is adapted to allow for cooling of the vessel walls and dissipation of any gas bubbles in blood caused by the pulsed laser treatment.

The disadvantages of such pulse-and-retreat techniques are that they are time-consuming, it is difficult to effectively position the working end in relation to the thrombus prior to the initial lasing session, and it is even more difficult to position the working end prior to follow-on lasing "sessions." (See, e.g., Topaz et al., "Acute Results, Complications, and Effect of Lesion Characteristics on Outcome with the Solid-state, Pulsed Wave, Mid-Infrared Laser Angioplasty System," *Lasers in Surg. & Med.* 22:228–239 (1998). Further, some such laser angioplasty treatments generally rely on photothermal absorption within the high water content of the thrombus itself to disrupt the thrombus.

It would be preferable to not deliver such excessive thermal effects to intraluminal fluids and to the thrombus. In using ultrasound catheters for blood clot disruption, it is believed that an ultrasonic "radiator" comprising a piezoelectric crystal or elongate tuned member cannot easily be miniaturized to the size needed for the brain's circulatory arteries and still deliver significant acoustic power. (Cf. U.S. Pat. No. 5,318,014 to Carter titled "Ultrasonic Ablation/Dissolution Transducer").

What is needed is a micro-catheter and working end: (i) that can be miniaturized to be easily introduce into 1 mm to 3 mm brain circulatory arteries either independently or over a guidewire; (ii) that has a lumen together with pharmacologic agent dosimetry control means for controlled delivery of such agents directly to the thrombus site; (iii) that has pharmacologic agent pressure delivery means for creating pressure gradients for such agent delivery into the working end and against thrombus; (iv) that carries acoustic-energy generation means for delivering acoustic energy against thrombus; (v) that includes control systems for modulating all parameters of both pharmacologic agent delivery pressure and acoustic energy propagation; (vi) that protects the endothelium and vessel walls from thermal damage; (vii) that protects the endothelium and vessel walls from acoustic damage while at the same time dissolving thrombus; (viii) that can be activated in a continuous mode while advancing the working end toward and through the thrombus to require less precision in the imaging component of a thrombolysis procedure; (ix) that utilizes a non-complex energy source such as electrical discharge instead of a laser source or an ultrasound generator; and (x) that provides a system with disposables that are simple and inexpensive to manufacture.

SUMMARY OF THE INVENTION

The present invention comprises a micro-catheter system that utilizes pulsed electrical discharges between first and second electrodes disposed within a recessed bore of the catheter working end. The microjoule discharges are adapted to expand gas bubbles that rapidly collapse into a cavitating volume of an electrolytic fluid composition including a pharmacologic agent AG introduced into the working end from a computer-controlled source.

The expansion and collapse of such gas bubbles at a high repetition rate will create acoustic waves that propagate distally from the working end of the micro-catheter to disrupt thrombus. The expansion and collapse of such cavitation bubbles also will project or "jet" the pharmacologic agent at a controlled velocity into the acoustically disrupted thrombus to further depolymerize the thrombus allowing it to flow through the patient's circulatory system.

The catheter system includes a computer-controller and various subsystems that allow for independent modulation of (i) all aspects of harmacologic agent delivery, and (ii) all parameters of electrical discharge to "tailor" the combined acoustic wave effects and pharmacologic agent effects to dissolve thrombus rapidly since the passage of time is critical in treating victims of stroke. It is believed that there are wide variations in thrombus size, location and other patient-specific characteristics that will require many different treatment parameters, which are offered by the control systems of the invention.

With respect to pharmacologic agent delivery, the system allows modulation of the dose of pharmacologic agent, the pressure or velocity of agent propagation into thrombus, and the timing of agent introduction relative to the actuation acoustic waves for disrupting the thrombus. With respect to the electrical discharge source, the computer controller and software can independently modulate voltage, peak power per pulse, discharge pulse length, the energy profile within each discharge pulse, and the timing between discharge pulses resulting in a set or variable discharge pulse rate.

BRIEF DESCRIPTION OF THE DRAWINGS

FIG. 3A showing the typical isotherms at about the instant of electrical discharge which creates a gas bubble; FIG. 3B showing isotherms ns following the discharge when the gas bubble collapses into a cavitating volume and being ejected from the confinement of the recessed lumen; FIG. 3C showing isotherms several ns later with the cavitating volume being further elected and cooling significantly.

FIG. 6A being the working end advancing toward the thrombus; FIG. 6B being the working end after the start of introduction of an electrolytic pharmacologic agent into the working end; FIG. 6C being the working end at about the instant of electrical discharge showing acoustic energy delivery to disintegrate thrombus; FIG. 6D being the working end at ns after FIG. 6C showing the combination of acoustic energy delivery and pharmacologic agent jetting against the thrombus and the technique of "continuously" operating the acoustic and agent delivery systems while advancing the working end through the dissolving thrombus.

DETAILED DESCRIPTION OF THE INVENTION

1. Type "A" Embodiment of Micro-Catheter

Figure 1:
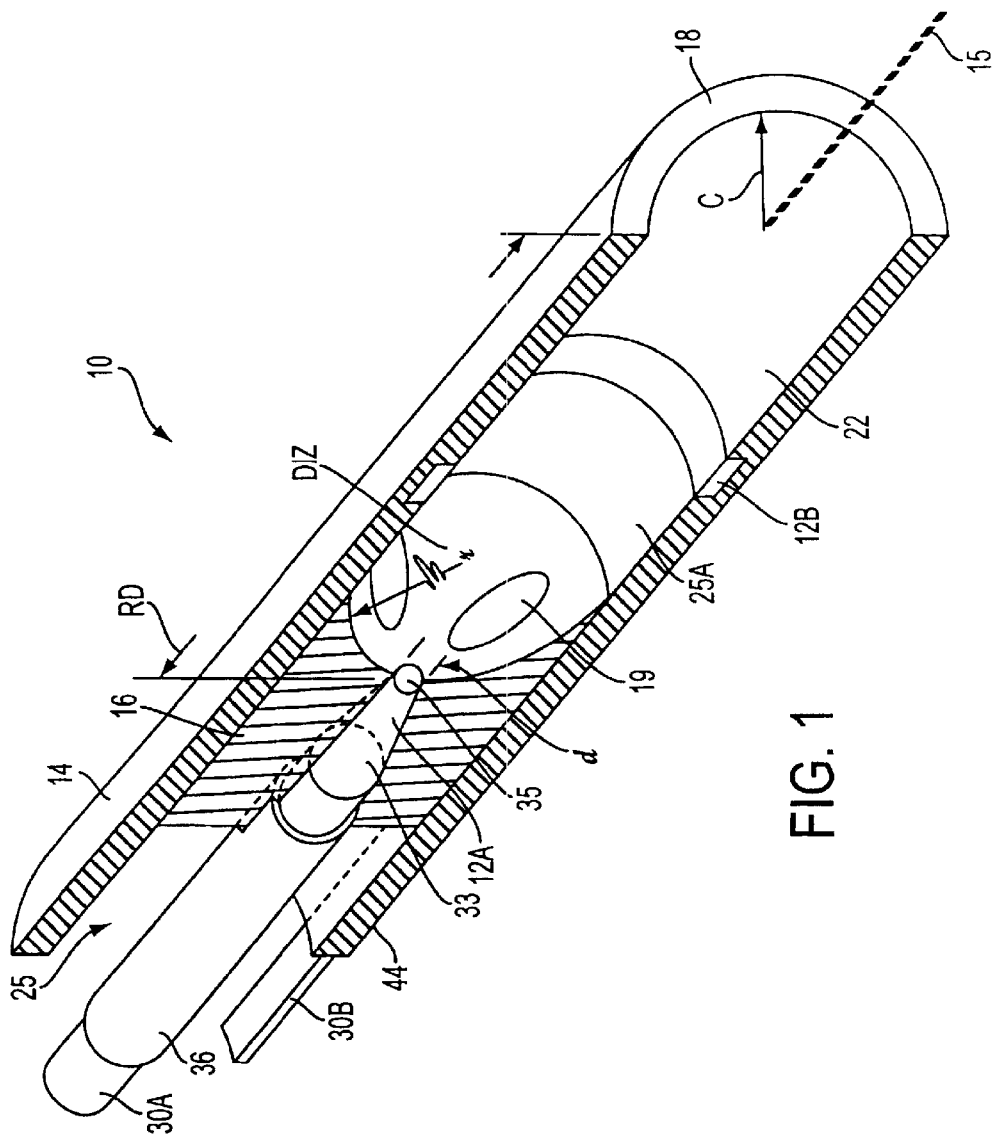
FIG. 1 is an enlarged sectional perspective view of a Type "A" micro-catheter working end of the invention showing the pharmacologic agent delivery lumen and first and second electrode geometry.

Referring to FIG. 1, the present invention comprises a micro-catheter system 5 having a body diameter of from 0.5 mm to 2.5 mm (not limiting) adapted for insertion into and through blood vessels as small as 1 mm for accessing the site of thrombus in circulatory arteries of the brain of a stroke patient. In FIG. 1, the working end 10 of micro-catheter 5 is shown that carries an electrode arrangement with first and second electrodes 12A and 12B for pulsed electrical discharges therebetween.

The electrical discharges are adapted to develop and expand gas bubbles BB that collapse into a cavitating volume CV within ane electrolytic fluid composition EF including a pharmacologic agent AG introduced into the working end. The expansion and collapse of such gas bubbles at a repetition rate creates acoustic waves that propagate distally to disrupt or disintegrate thrombus. (The terms disrupt, disintegrate and fragment in relation to thrombus may be used interchangeably in this disclosure and are defined as meaning the reduction of a thrombus mass into a particulate-sized composition that will flow along with blood through the patient's circulatory system.)

The rapid expansion of such gas bubbles further develops pressure gradients in the cavitating volume of the electrolytic fluid EF to thus project or "jet"the cavitating volume CV at suitable velocities relative to the working end 10 and against and into acoustically-disrupted thrombus.

The catheter body or sleeve 14 is elongate and has any suitable length along centerline 15 (FIG. 1). The catheter body 14 is of any suitable extruded plastic catheter material or other braided or composite material known in the art. FIG. 1 shows first (proximal) electrode indicated at 12A along centerline 15 in distal catheter core 16 that is carried at recessed dimension RD from the distalmost end or perimeter 18 of catheter body 14.

One or more fluid flow passageways 19 are provided through or around core 16 for allowing electrolytic fluid composition EF and pharmacologic agent AG flow therethrough. Catheter core 16, as can be seen in FIG. 1, has a concave-shape 20 facing distally for reasons described below. Second (distal) electrode 12B is shown as extending around the inner portion of walls 22 around the distal portion of the catheter lumen 25, or more particularly, the distal recessed lumen portion indicated at 25A. It should be appreciated that second electrode 12B may comprise one or more separate electrode elements around the distal portion or end of catheter body 14.

Referring still to FIG. 1, it can be seen that the concave-shape indicated at 20 may be of any suitable radius r given the small dimension of recessed lumen portion 25A and of catheter body 14. It should be appreciated that the radius r of concavity (e.g., the concavity may be almost flat or flat) is less important that the fact that concavity 20 is recessed in lumen portion 25A a particular recessed dimension RD which ranges from a maximum of about 10.0 mm to a minimum of about 0.5 mm. More preferably, the recessed dimension RD ranges from a maximum of about 5.0 mm to a minimum of about 1.0 mm.

The recessed core 16 (which carries first electrode 12A) together with recessed lumen 25A are adapted to serve several purposes that are described next, and in additional relevant detail in Section 2 concerning the technique of the invention. The electrical discharge between the first and second electrodes causes several energy "effects," each of which must be modulated to achieve dissolution of thrombus while at the same time not damaging the endothelium EN or vessel walls 28 (see FIG. 2A).

The energy "effects" resulting from a single electrical discharge, or preferably a sequence of pulsed discharges, in an electrolytic fluid medium in which the working end is immersed are: (i) the electro-mechanical (or hydraulic) effects which result in acoustic waves propagating within intraluminal fluids of a vessel; (ii) electro-thermal effects in the electrolytic fluid; and (iii) cavitation and propagation of fluids at high acceleration rates and fluid flow velocities away from the site of the electrical discharge.

Figure 2A:
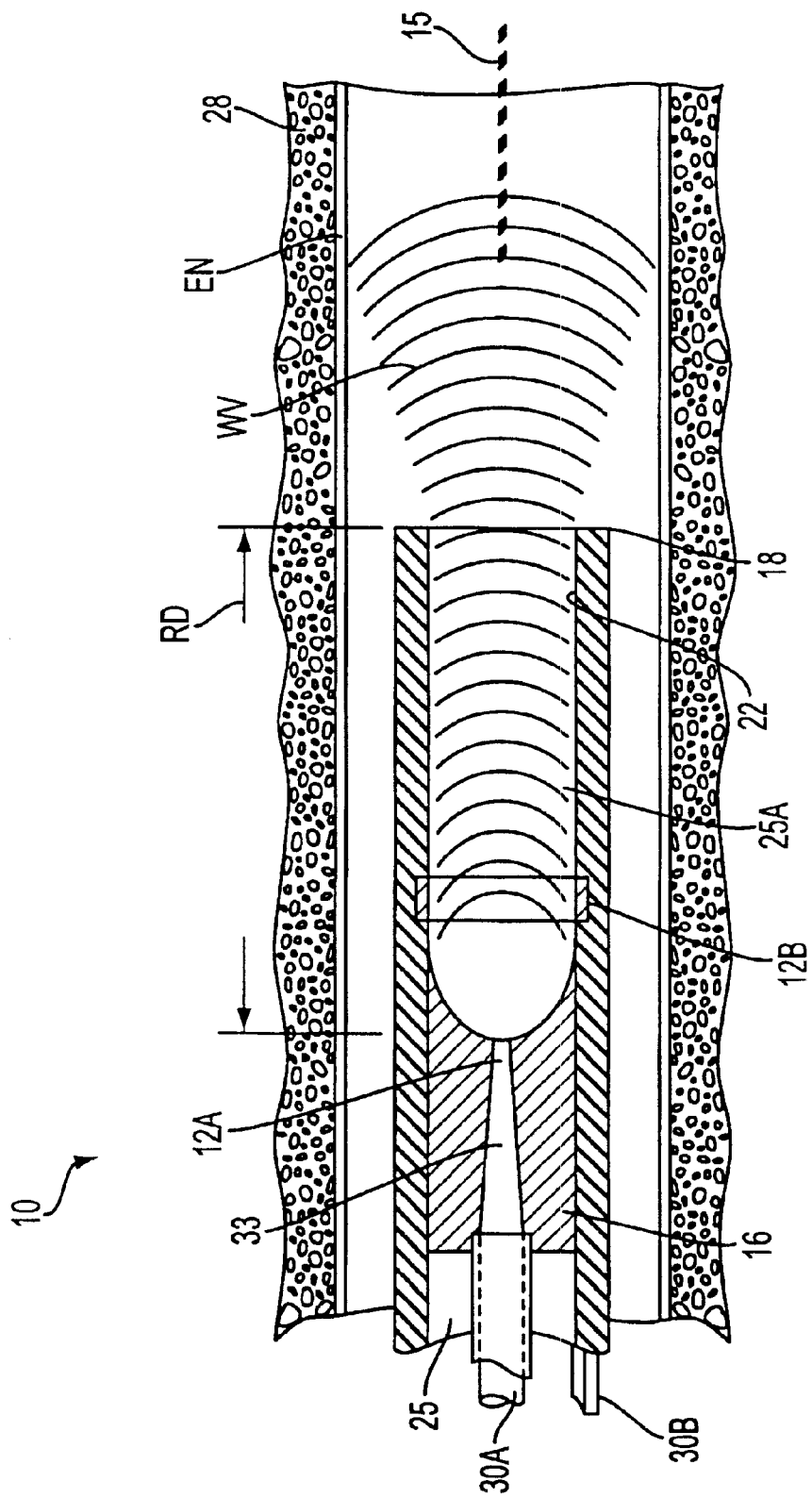
FIG. 2A is a sectional view of the working end of FIG. 1 illustrating that the recessed distal lumen will induce the propagate of acoustic waves generally axially in a vessel lumen rather than against the endothelium of the vessel.

A first purpose for core 16 being recessed dimension RD is to provide means for directing acoustic wave propagation. Referring to FIG. 2A, acoustic waves WV are generated by the expansion and collapse of a gas bubble BB in contact with electrode 12A at the time of an electrical discharge. As will be described below, acoustic waves of a suitable frequency, either pulsed or continuous, can disrupt or fragment thrombus (cf. U.S. Pat. No. 5,424,620 to Rosenschien titled "Ablation of Blood Thrombi By Means of Acoustic Energy").

The extension of recessed lumen portion 25A distally from electrode 12A is adapted to initially confine the expansion and collapse of gas bubbles to the working end. Such confinement within the walls 22 around lumen 25A thus direct all hydraulic forces and acoustive wave forms WV generally axially and distally along axis 15 as indicated in FIG. 2A. In other words, the propagation of such waves within intraluminal fluids (e.g., blood or an introduced fluid) will be generally "along" the vessel walls 28 instead of more directly against the vessel walls.

Figure 2B:
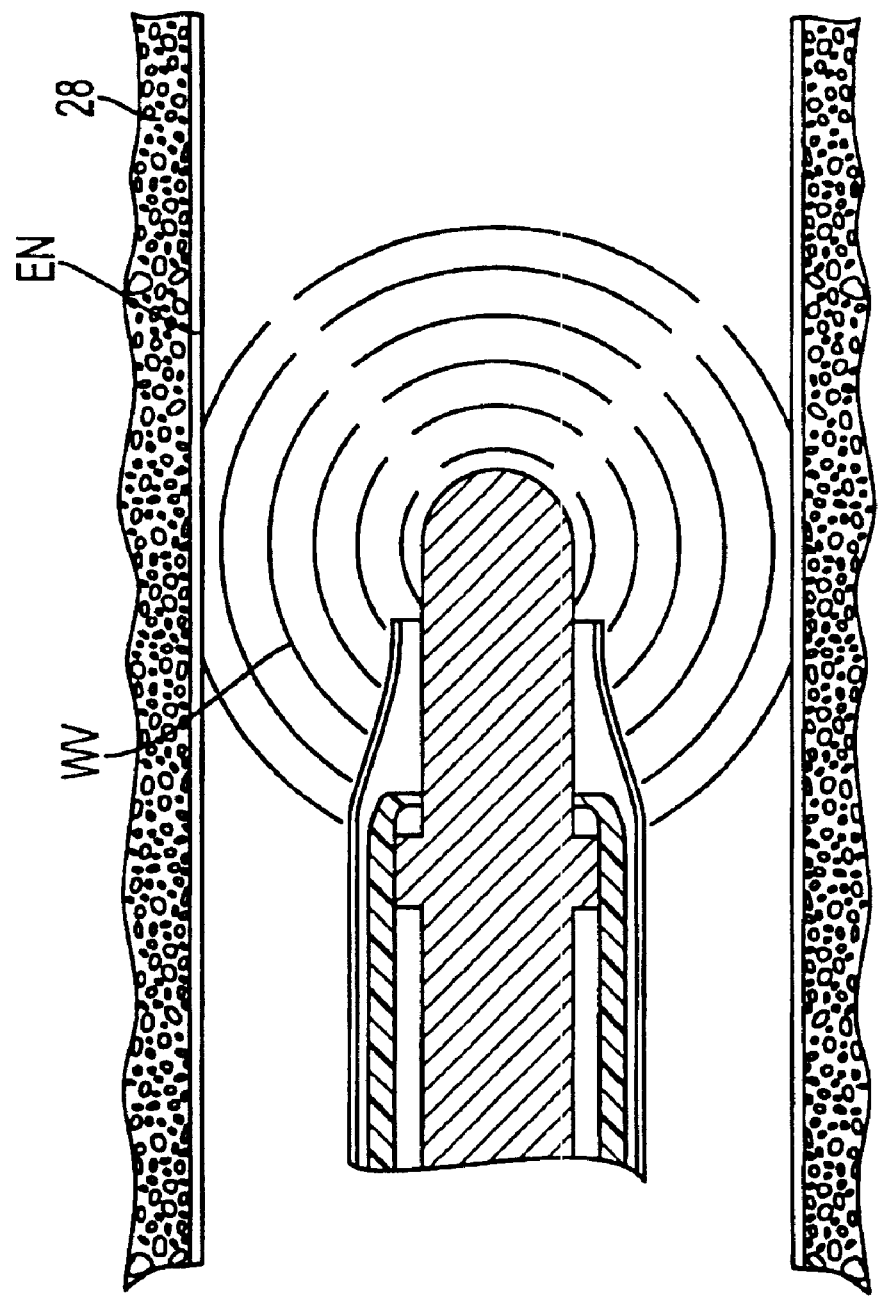
FIG. 2B is a prior art ultrasound "radiator" that propagates acoustic waves at all angles including direct angles against the vessel walls such that the endothelium may be damaged.

Such an axial propagation of wave forms WV is important because damage to the endothelium EN or perforation of the vessel wall could result in a life-threatening complication. The "along-the-lumen" acoustic wave propagation that is provided by the working end 10 of the invention is to be contrasted with the prior art ultrasound catheter of FIG. 2B in which the exposed "radiator" may propagate acoustic waves at more direct angles against the vessel walls and thus have a higher probability of damaging the endothelium EN or bursting the vessel wall.

A second purpose for core 16 and first electrode 12A being recessed dimension RD is to provide thermal-effect dissipation means to eliminate the possibility of tissue damage from thermal effects caused by the electrical discharge. It is an objective of the invention to dissolve thrombus without relying on thermal energy being applied to the thrombus itself. For this reason, the extended lumen portion 25A of the above described dimensions is provided to largely confine thermal effects to the introduced electrolytic fluid composition EF (or blood) between electrodes 12A and 12B. Thus, thermal effects will not be in close proximity to the endothelium EN or vessel walls 28.

Figure 3A:
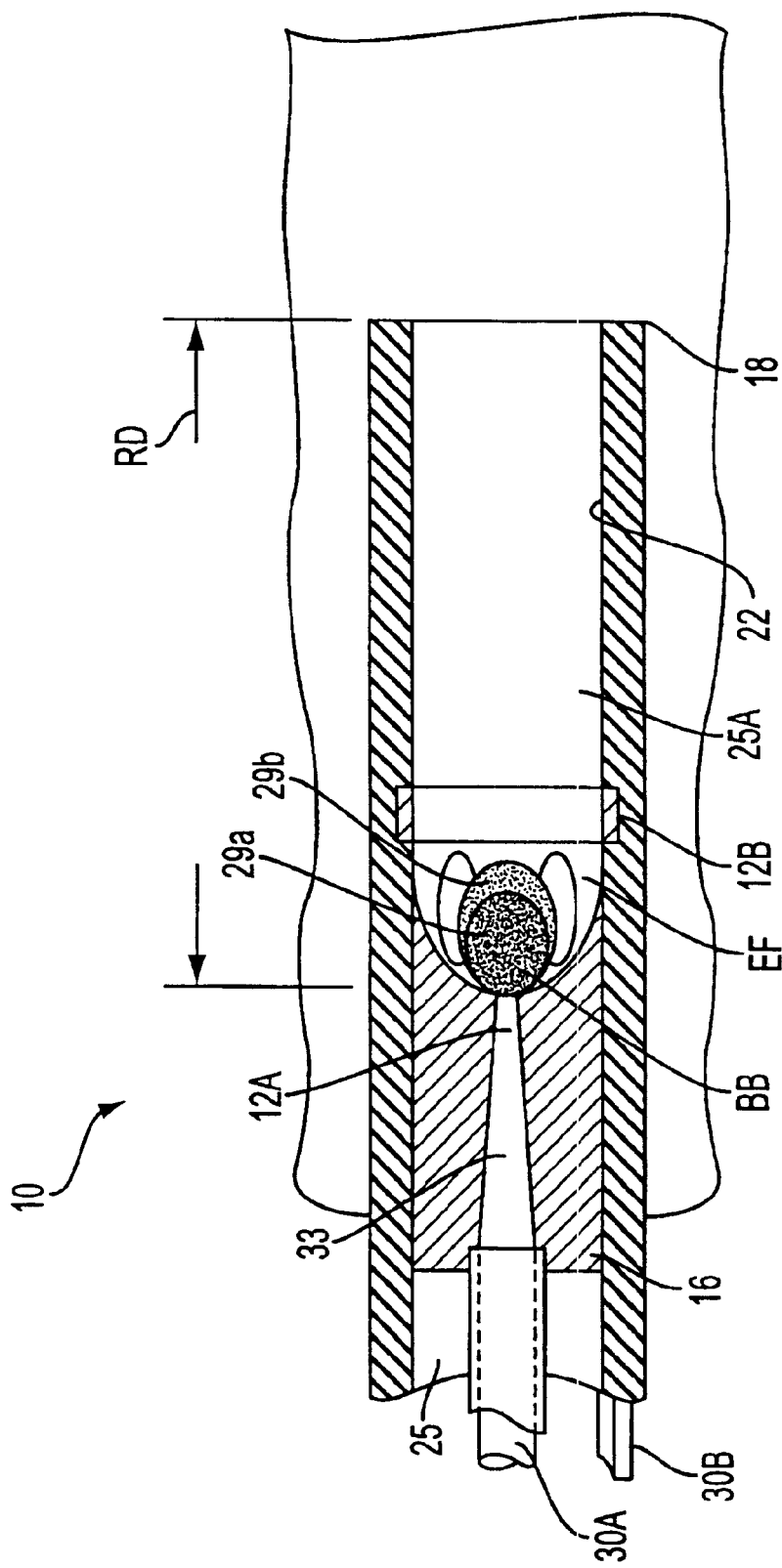
FIGS. 3A–3C are sectional representations of working end of FIG. 1 in a vessel lumen showing isotherms created in intraluminal fluids over a period of milliseconds following an electrical discharge between the first and second electrodes.
Figure 3B:
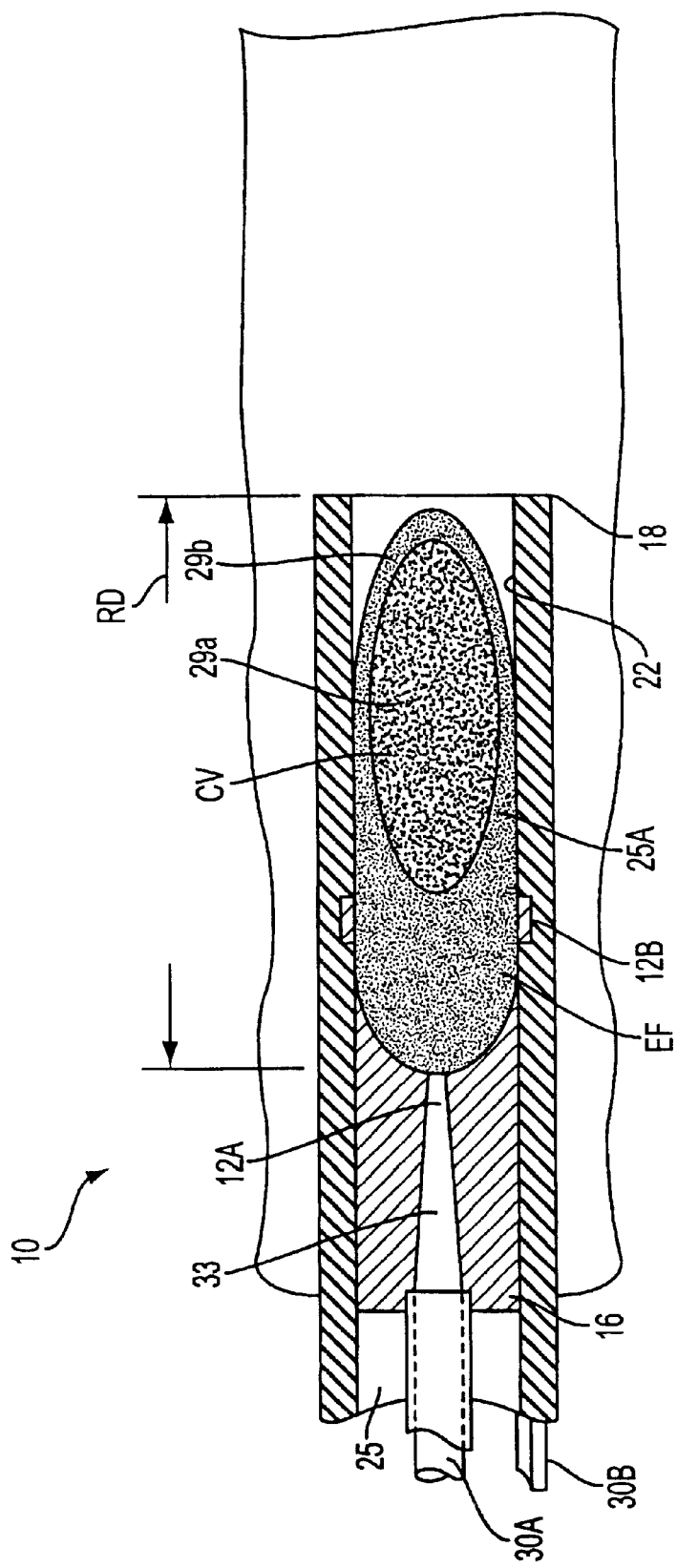
Figure 3C:
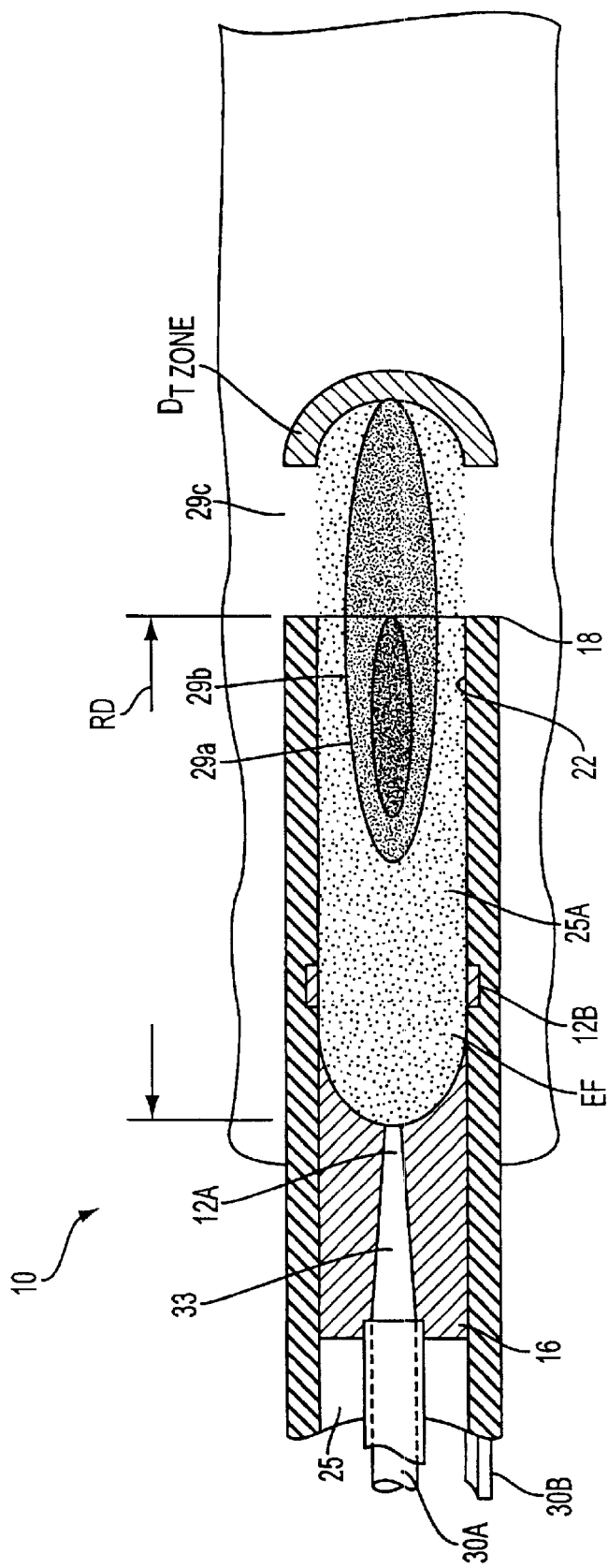

Referring to FIGS. 3A–3C, representations of isotherms 29a–29c are shown within and around working end 10 in electrolytic fluid EF and indicate temperature levels in the fluid in which the working end 10 is immersed. The views of FIGS. 3A–3C are at various arbitrary nanosecond (ns) intervals after an electrical discharge between electrodes 12A and 12B. The temperature levels within the isotherms 29a–29c are arbitrarily labeled with the darkest shading indicating a "tissue-ablative" temperature range, the medium shading being a temperature range that has "no effect" on tissue.

FIG. 3A represents fluid EF within at the time of an electrical discharge (at time=$T_{ZERO}$) showing the superheating of the electrolyte to about 100° C. in contact with electrode 12A and the formation of a gas or cavitation bubble BB which comprises the highest temperature zone and which would ablate the endothelium EN if in contact with it.

FIG. 3B represents the effect of the discharge a few ns later (at time=$T_{+1a.u.}$ where a.u. is an arbitrary unit of time) at which time the cavitation bubble BB would collapse into a volume of smaller cavitating bubbles (not shown; hereafter cavitating volume CV) with the superheated area expanding and moving away from electrode 12A caused by pressures related to the bubble expansion and collapse.

FIG. 3C represents the effect of the electrical discharge a few ns later (at time=$T_{+2a.u.}$) wherein the superheated region has moderated in temperature as the cavitating volume CV expands further and is projected distally from the working end of the catheter. Thus, it can be seen in FIG. 3C that the endothelium EN and vessel walls 28 can be protected from thermal effects by confining the electrolytic fluid EF when superheated to recessed lumen portion 25A. By the time that the electrolytic fluid EF is ejected from the lumen portion 25A, it is believed that the dimension RD of lumen 25A will allow for cooling of the cavitating volume to a non-damaging temperature. For this reason, a time-temperature gradient can be developed which will show a dissipation-of-temperature zone indicated at shaded region $D_T$ wherein the temperature of the fluid EF would be cooled below the threshold level that would damage tissue.

As will be described below in the technique of the invention, all energy delivery parameters (voltage, current, discharge rate, electrolytic level of fluid, etc.) will be tested in various combinations to place $D_T$ zone at a suitable location at or about the distal end 18 of the catheter.

A third purpose for working end core 16 being recessed by dimension RD is to provide fluid-velocity dissipation means for reducing the velocity of fluid jetting from working end 10 to a suitable velocity that will not "cut" tissue. The extended lumen portion 25A is provided as a region of confinement within the device in which the acceleration in propagation of the cavitating volume CV is slowed such that it will not contact the endothelium EN at any particular high velocity that would cut the endothelium.

It should be understood that the velocity of propagation of the cavitating volume CV (including pharmacologic agent AG) relates to (i) the pressure under which the fluid is introduced, and (ii) the expelling forces created by the expansion and collapse of gas bubbles. Further, the jetting velocity of the cavitating volume into the interface of intraluminal fluid (blood) makes somewhat unpredictable the actual distal movement of the cavitating volume CV. In any event, the velocity of propagation of the cavitating volume CV is different from the speed of propagation of acoustic waves WV therein which propagate across the interface between the introduced fluid EF and the pre-existing intraluminal fluids (blood).

The objective of the working end of the present invention is to create a flow velocity in the cavitating volume, which includes the introduced pharmacologic agent AG, to engulf the thrombus instantly after the acoustic waves have struck and disrupted the thrombus. At the same time, the flow velocity must not be so high as to cut tissue. As is well known in field of laser-tissue interactions, such soft tissue cutting occurs when short laser pulses causes the explosive expansion of media absorbing photonic energy in close proximity to tissue, or within fluids in the tissue surface itself, thus creating cavitation within the media or tissue.

In such laser-tissue interactions, any soft tissue proximate to the expansion and collapse of such bubbles will be disrupted or "cut." A similar cutting process could occur with the fast electrical discharge between electrodes 12A and 12B of the working end 10 disclosed herein if any such tissues were proximate to first electrode 12A. Since the objective of the present invention is to not cut tissue, it is necessary to insure that thrombus T and the vessel walls 28 are maintained at a particular desired distance from the cavitating volume CV and its distal projection at particular velocities.

Figure 4:
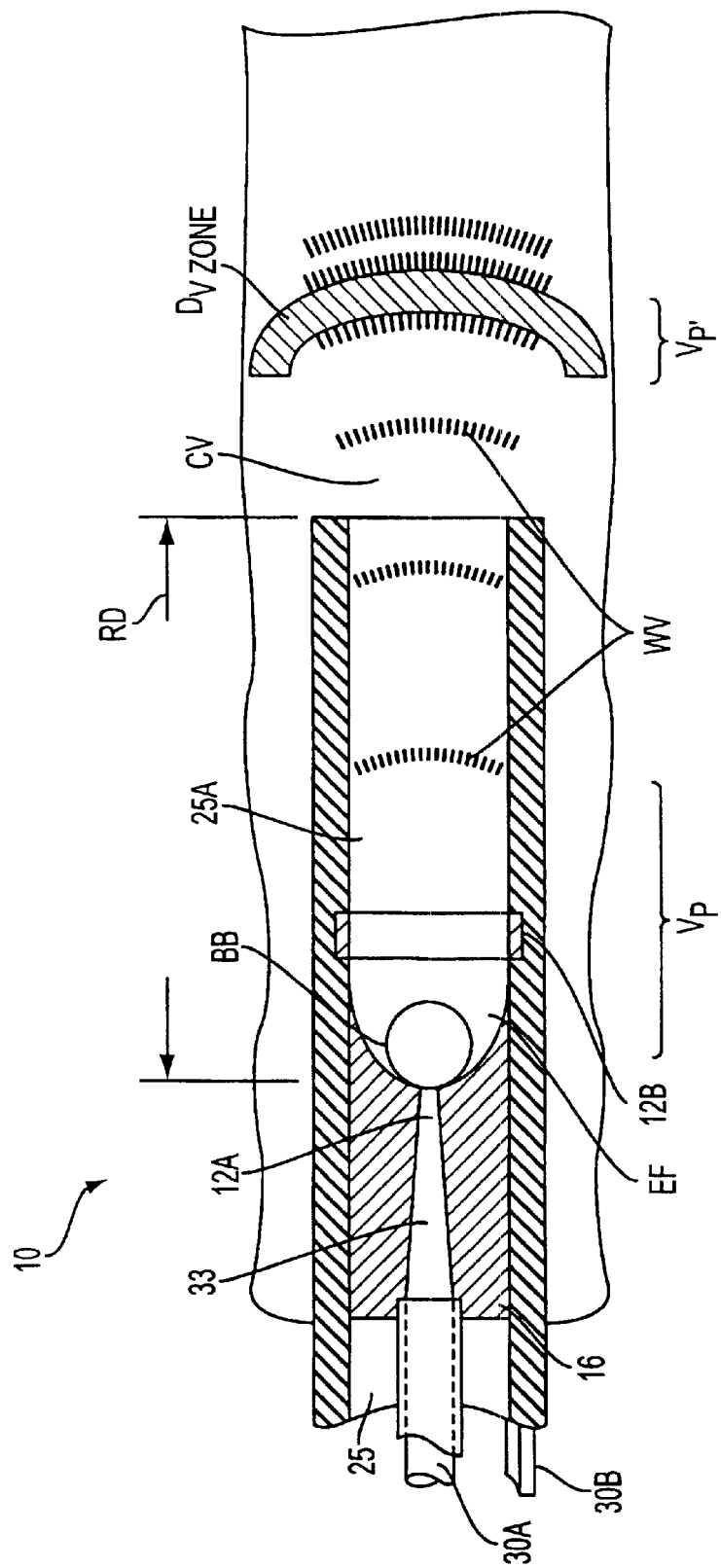
FIG. 4 is a sectional representation of the working end of FIG. 1 in a vessel lumen showing velocities of ejection of an introduced fluid over a period of milliseconds following an electrical discharge between the first and second electrodes.

As shown in FIG. 4, the velocity of propagation $V_P$ of the cavitating volume or agent AG is generally indicated by wave forms WV. The distance between wave forms indicates velocity, or the distance traveled per arbitrary unit of time, which diminishes as distance increases from the location of bubble formation at electrode 12A. FIG. 4 thus indicates that initial VP close to electrode 12A will diminish to lesser $V_P'$ just beyond the distalmost end 18 of the catheter. It can be thus understood that electrode 12A and extended lumen portion 25A are provided to insure that tissue is not in close proximity to a cavitating volume CV when it is traveling or jetting distally at initial VP which could cut tissue.

Still, thrombus T contacted by the cavitating volume CV at diminished velocity $V_P'$, in addition to being subjected to acoustic wave forces sufficient to fragment thrombus T, will be engulfed in chemical lysis effect of the pharmacologic agent AG within the cavitating volume CV as described below. For this reason, a time-velocity gradient can be developed to identify a dissipation-of-velocity zone indicated at shaded region $D_V$ wherein the velocity of electrolyte or agent jetting would be below the threshold level that would "cut" tissue. The discharge parameters (voltage, current, discharge rate, electrolytic level of fluid, etc.) will be tested in combinations to place $D_V$ zone at a suitable distance from the distal end 18 of the catheter.

A fourth purpose for the recessed dimension RD of core 16 is to provide a confinement zone or discharge interaction zone DIZ in which the inner surfaces of walls 22 around recessed lumen portion 25A are adapted to capture the introduced electrolytic fluid EF between electrodes 12A and 12B. By this means of largely capturing the electrolytic fluid EF momentarily before it intermixes with the pre-existing intraluminal fluids, it is possible to accurately predict and model the effects of the electrical discharge since the electrolytic characteristics of the electrolytic fluid EF can be pre-determined. This is to be contrasted with a situation in which no means would be provided for confining a known electrolyte between the electrodes and the discharge would occur in blood or a mixture of blood and introduced fluids, in which case the effects would be unpredictable.

A fifth purpose for working end core 16 being recessed by dimension RD is to provide electrical discharge confinement means for reducing the threshold energy levels required to induce cavitation bubble formation—that is, to increase energy efficiency. It is postulated that the threshold for bubble generation per electrical discharge (and thus acoustic wave propagation) will be in the range of about 1 $\mu$J to 50 $\mu$J which may be significantly less than used in laser-based catheters developed for angioplasty purposes. (As described below, a somewhat broader range of $\mu$J energy delivery is disclosed to perform the technique of the invention.) It is believed that the faces of walls 22 around recessed lumen portion 25A and the capture of the expanding bubble volume will create additional pressures on the bubble formation and thus lower the threshold energy discharge requirement, in contrast to a situation in which no such confinement was provided.

Figure 5:
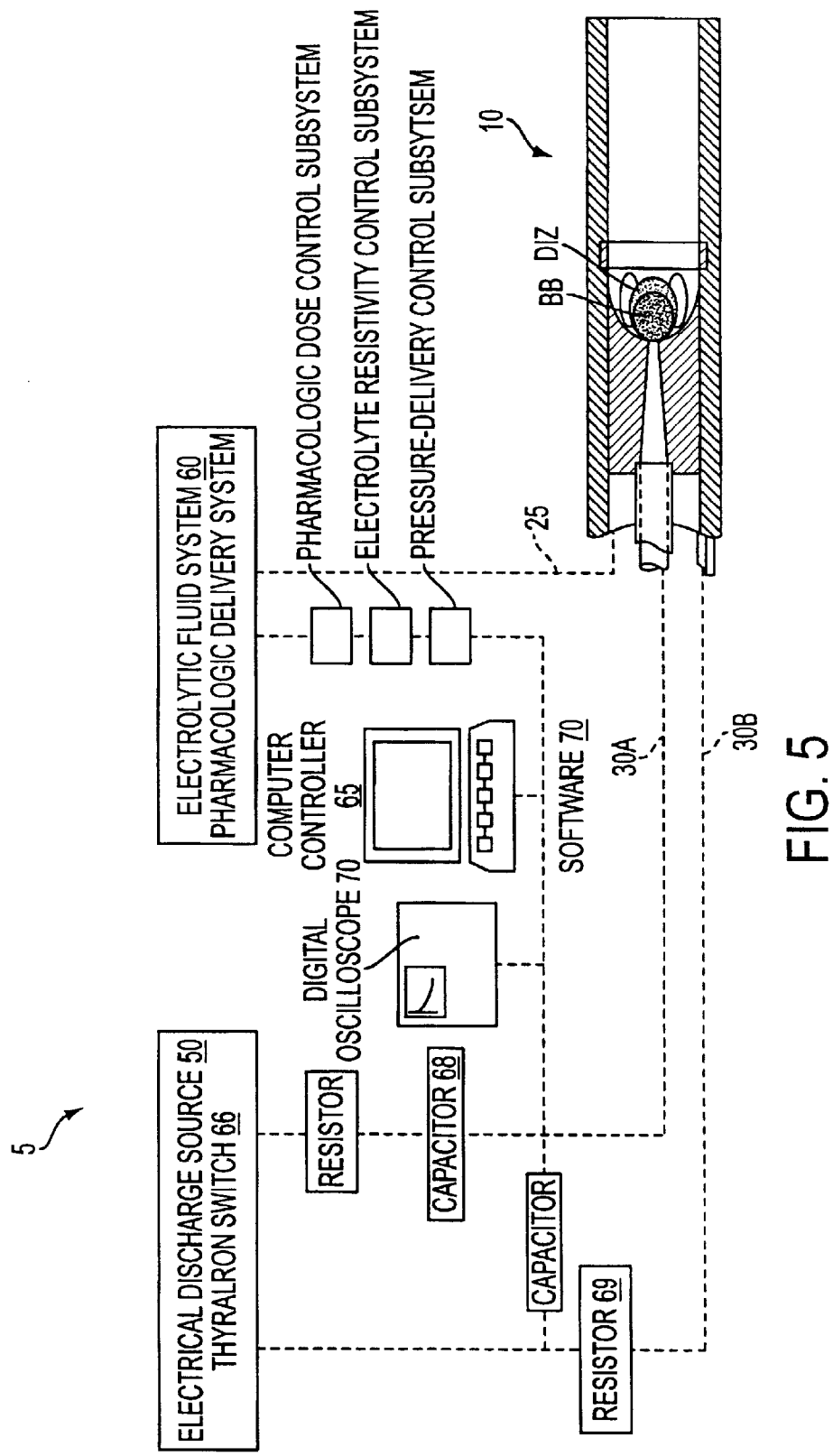
FIG. 5 is a schematic view of the electrical discharge source and pharmacologic agent delivery source of the invention, together with computer-control systems for modulating all parameters of combined electrical discharge and agent delivery to optimize thrombus dissolution.

Referring to FIGS. 1 and 5, first proximal electrode 12A is coupled to the distal end of conductive wire or element 30A that extends through lumen 25 of catheter body 14. The recessed catheter core 16 is bonded or molded in place within lumen 25 of the catheter with electrode 12A molded or inset therein. To catheter distal core 16 may be any suitable insulated material such as a plastic or glass-type compound.

First electrode 12A, as can be seen in FIG. 1, has a significantly reduced cross-section portion 33 such that the exposed electrode surface portion 35 that is exposed to a discharge in recessed lumen 25A has a very small diameter d (e.g., ranging in diameter from about 5 microns to 25 microns or equivalent cross-section). The exposed surface area 35 preferably is from about 0.05 mm$^2$ to 0.5 mm$^2$ and thus causes the energy discharge to be focused about a very small surface area within the discharge interaction zone DIZ.

FIG. 1 shows that wire 30A with insulation 36 may be carried loosely and lumen 25 of catheter sleeve 14 making the catheter simple to fabricate. Current-carrying wire 30A may be any suitable conductive material, for example platinum, copper, gold, etc. In FIG. 1, it can further be seen that the medial portion of catheter body 14 has wall portion 44 with current-carrying flat wire 30B embedded therein which extends to second electrode 12B. The thickness of wall 44 may be any suitable dimension.

Wires 30A and 30B may be any diameter from about the 10 to 200 microns in diameter or equivalent cross-section. The axial dimension between first electrode 12A and second electrode 12B ranges between about 0.1 mm and 10.0 mm, along with a lumen cross-section indicated at C in FIG. 1 ranging between 0.2 mm and 2.0 mm in diameter or equivalent cross-section, thus creating a particularly dimensioned discharge interaction zone DIZ.

FIG. 5 is a schematic view of the catheter system 5 showing electrical discharge source 50 and the electrolytic fluid composition EF and pharmacologic agent AG delivery system 60 that are connected to working end 10 and lumen 25 at a catheter handle portion (not shown) by means known in the art. Typically, the fluid composition EF including agent AG are intermixed to provide a known electrolytic component (i.e., with known resistivity (Ohms/cm.), heat capacity (J/g.), etc.).

The fluid delivery system 60 includes a manual control or preferably is controlled by a computer-controller known in the art and indicated at 65 to release the fluid from a reservoir operatively connected to the catheter handle. As can be seen in FIG. 5, the computer controller 65 coupled to the fluid delivery system 60 allows independent modulation of all elements of electrolytic fluid EF delivery through subsystems, including: (i) the dose of pharmacologic agent AG per volume of fluid EF; (ii) the electrolytic component (current-resisting or sensitizing composition yields resistivity of fluid EF in Ohms/cm.) of the fluid EF; (iii) the particular pressure of flow of fluid EF through the catheter and working end; and (iv) the timing of fluid EF introduction relative to the actuation of a pre-determined sequence of electrical discharges from electrical discharge source 50.

The electrical discharge source 50 of the invention also is shown in FIG. 5 and is based on a thyratron switch 66 that can enable a very fast discharge of capacitor 68. After the thyratron is switched on, and following a very short rise time, an electrical discharge pulse will be generated between first electrode 12A and second electrode 12B that results from the discharge of the capacitances through the electrolytic fluid EF that has flowed into distal lumen portion 25A and in which the discharge interaction zone DIZ is thus immersed.

The electrical discharge source 50 and the wires 30A and 30B will have some capacitance which will result in the voltage at the electrodes 12A and 12B to be somewhat less than the starting voltage at capacitor 66. Still referring to FIG. 5, with the thyratron 66 switched off, the capacitor 68 will charge back to its potential through a second resistor and through the electrolytic fluid in which discharge interaction zone DIZ and working end 10 is still immersed. The electrical discharge source 50 is further coupled to computer controller 65 that may be programmed with suitable software 70 to independently modulate all parameters of energy levels and timing the electrical discharge, including: (i) voltage, current and peak electrical power per pulse; (ii) the length of a discharge pulse; (iii) the profile of energy within each discharge pulse, and (iv) the timing between discharge pulses resulting in a set or variable discharge pulse rate.

FIG. 5 shows that a digital oscilloscope 75 is between electrodes 12A and 12B to register the voltage and current pulses in association with computer controller 65.

2. Technique of Use of Type "A" Embodiment of Micro-Catheter

Figure 6A:
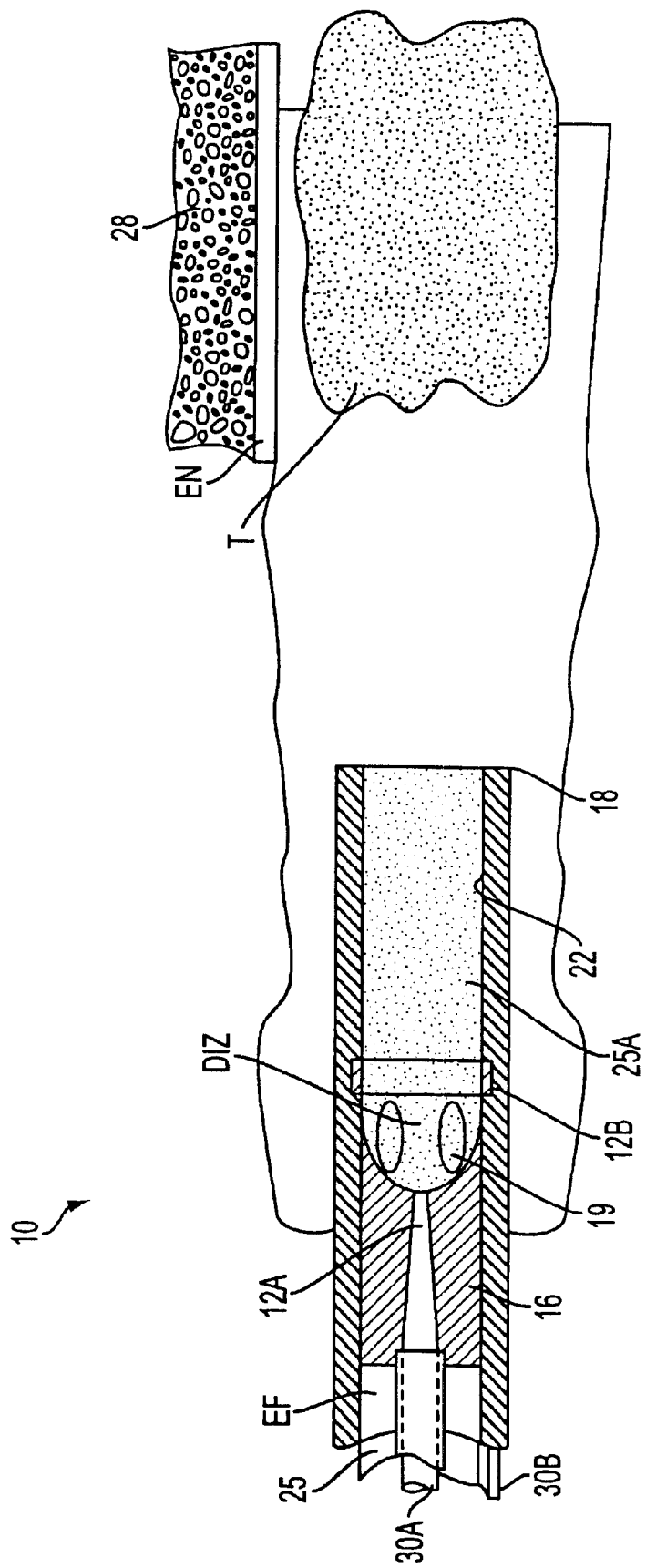
FIGS. 6A–6D are illustrations that represent the manner of using the micro-catheter of invention to perform the techniques of the invention in dissolving thrombus.

In use, the patient would be prepared in the usual manner and working end 10 of catheter 5 would be introduced to the site of the thrombus T in the blood vessel under any suitable imaging or angiography system. Referring to FIG. 6A, under such imaging, the working end 10 of the catheter would be advanced to within about 10 mm. or less from the location of thrombus T.

Figure 6B:
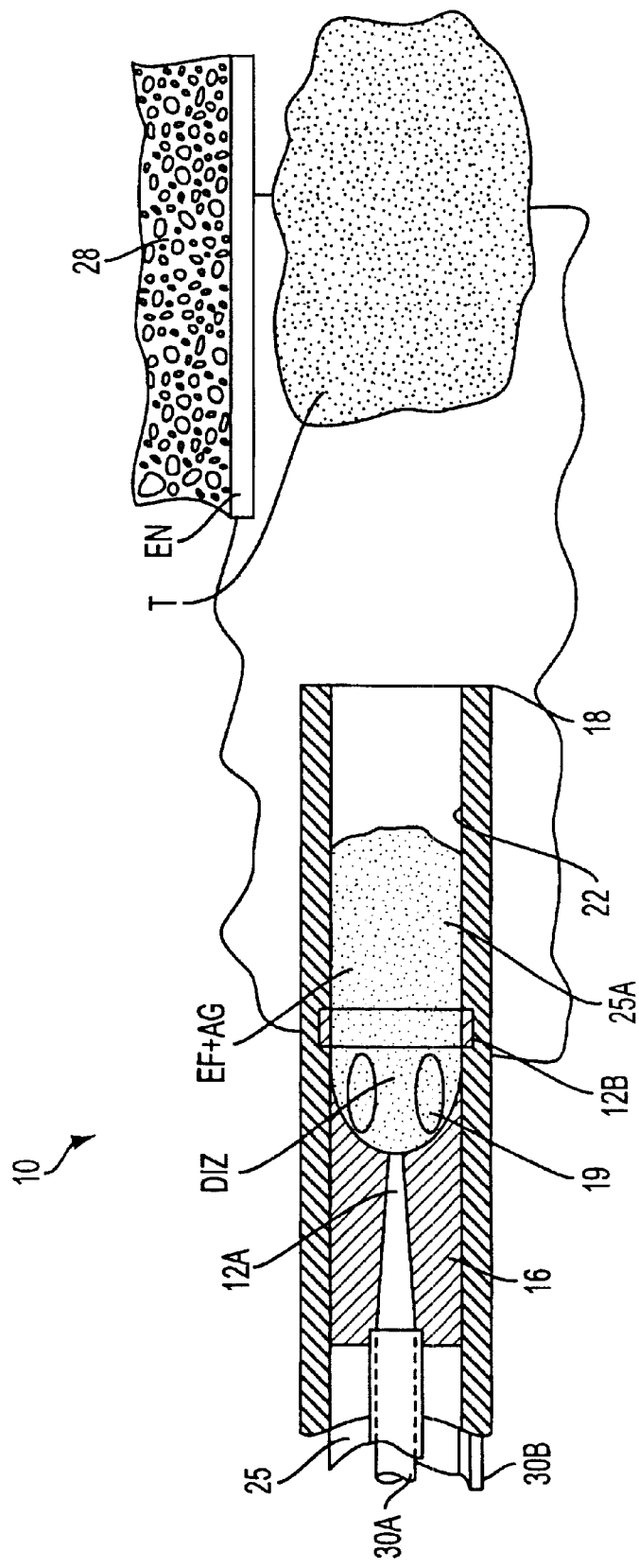

Next, referring to FIG. 6B, the controller 65 would be actuated (at time=$T_{ZERO}$) to deliver a predetermined dose of electrolytic fluid EF and pharmacologic agent AG through lumen 25 at pre-selected pressure into recessed lumen portion 25A at the working end 10 of the catheter. The composition of electrolytic fluid EF (e.g., saline solution) and pharmacologic agent AG would have been determined prior to treatment by modeling as described above. The pharmacologic agent AG is selected from a class of suitable thrombolytic agents known in the art, for example, including t-PA, streptokinase and urokinase.

Figure 6C:
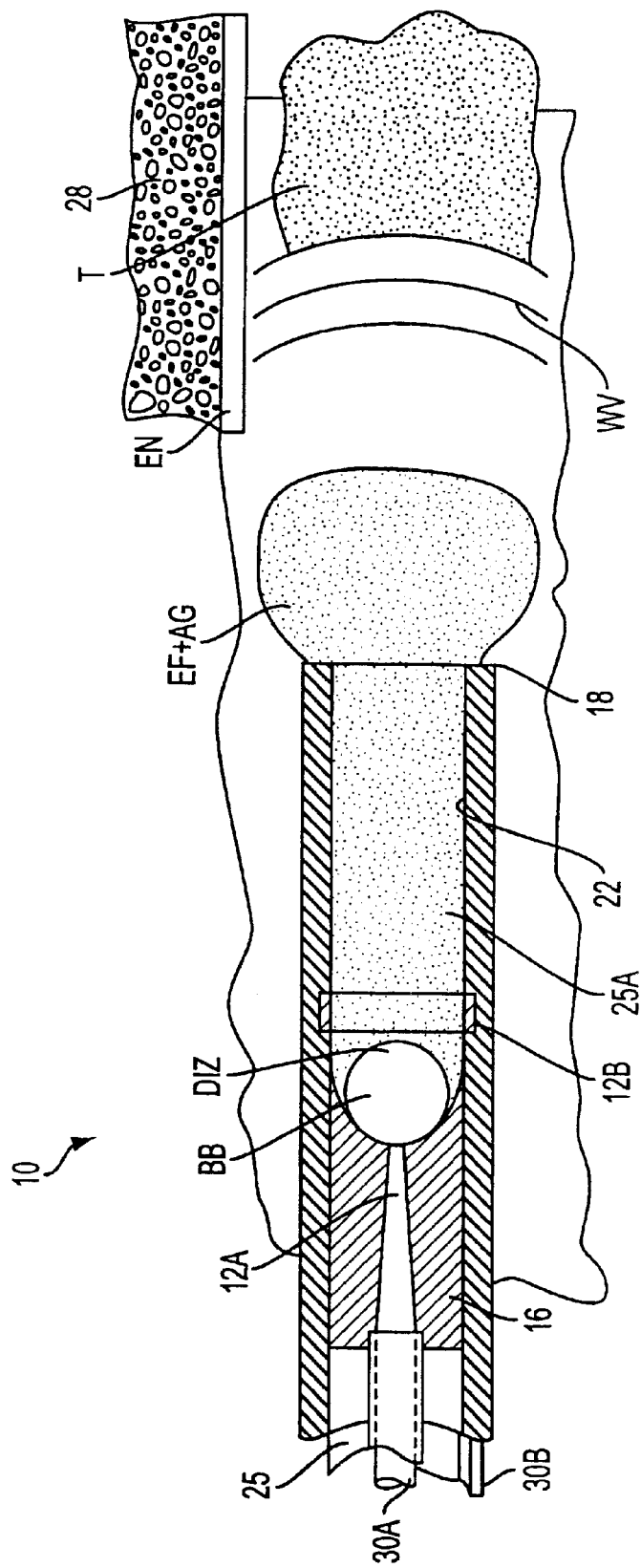

Now referring to FIG. 6C, at a certain time later (ranging from about a ms to 1 second) hereafter identified as an arbitrary unit of time a.u., the electrical discharge source 50 is actuated. FIG. 6B thus represents time=$T_{+1a.u.}$ when a first electrical discharge crosses the gap between first electrode 12A and second electrode 12B which superheats the electrolytic fluid EF in contact with surface area 35 of electrode 12A.

In a matter of nanoseconds or less, the discharge forms a cavitation bubble BB that expands in diameter from a few microns to about 500 microns or the size of the lumen. The expansion of the bubble within recessed lumen portion 25A will develop pressure waives or acoustic waves that will propagate distally within working end 10 and then through intraluminal fluid (e.g., blood) to strike the thrombus T as was illustrated in FIG. 2A). It is believed that the acoustic waves WV will resonate within the thrombus to thus disrupt or disintegrate the thrombus as shown in FIG. 6C. As also is shown in FIG. 6C, the expansion of the bubble BB causes the electrolytic fluid EF and agent AG to be ejected distally from the working end 10.

Figure 6D:
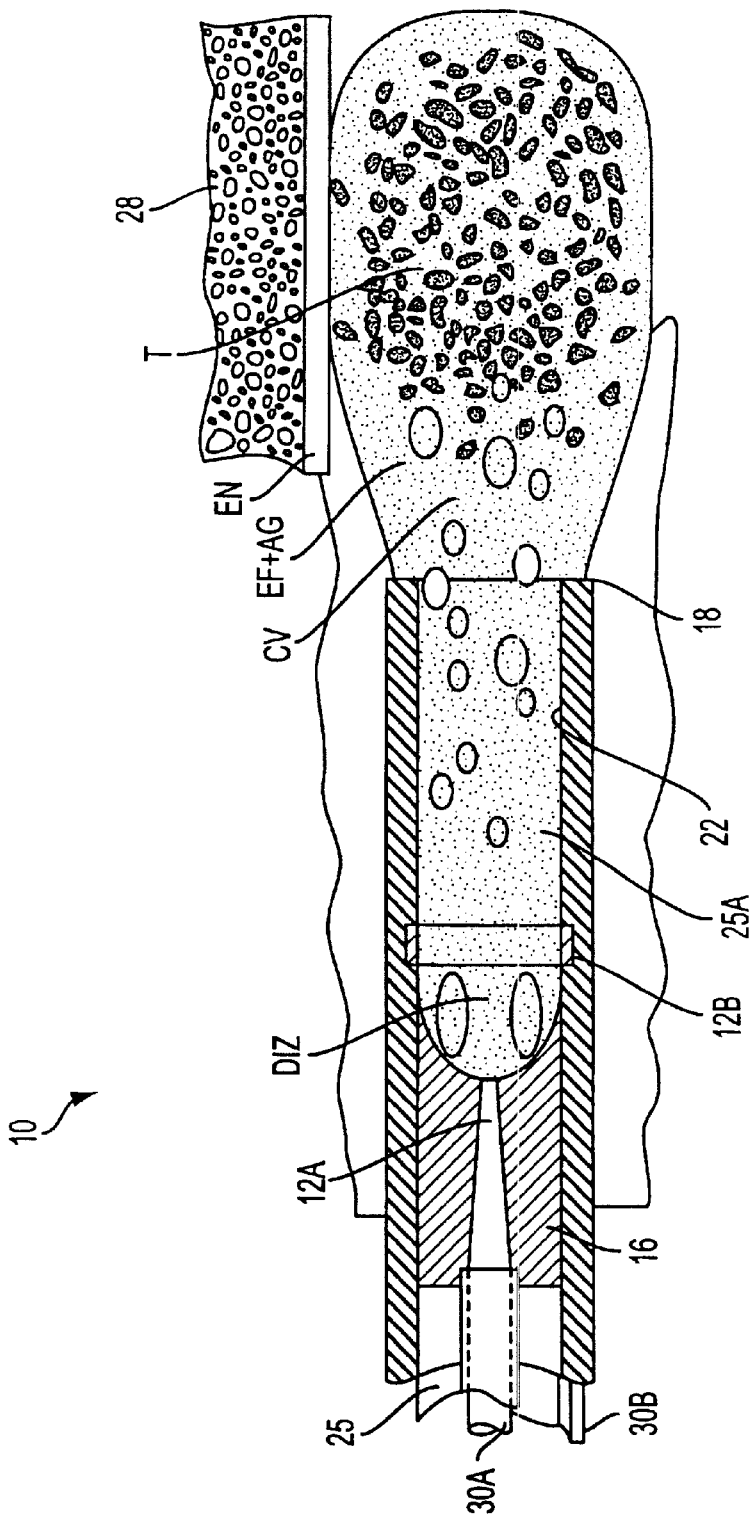

FIG. 6D at time=$T_{+2a.u.}$ represents the ejection or jetting of fluid EF and agent AG further to engulf the disintegrated or acoustically-disrupted thrombus T. It is believed that agent AG will be ejected distally with the velocity being enhanced by concave surface 20 such that the velocities within lumen 25A will range from about 1 to 25 m/s. As also shown in FIG. 6D, it is postulated that the energy parameters can be modulated to produce cavitation bubbles resulting from the collapse of initial bubble BB, and fluid velocities, that will dissipate entirely at distances ranging from about 0.1 mm to 5.0 mm from the distal end 18 of the catheter which would meet the objective of the invention. Not shown in FIG. 6D are follow-on pulsed electrical discharges that will repeat the process of acoustic wave generation and pharmacologic agent AG jetting.

By this combination technique, it is believed that pressure waves WV against the thrombus T followed by the immersion of remaining thrombus in the cavitating pharmacologic agent AG will dissolve the thrombus T rapidly and efficiently to a particulate dimension that will flow through the patient's blood vessel system. It is believed such a combination technique will offer better thrombolytic results than possible with the use of energy-delivery alone, or the use of pharmacologic agents alone.

The system disclosed herein is adapted to be tested with modulation of all electrical discharge parameters to define the optimal pulse rate for acoustic waves to disrupt thrombus, and the locations of dissipation zones as defined above to control fluid jetting velocities and thermal effects. Modeling suggests that the pulse energy that is optimal for thrombolysis, both for acoustic wave generation and fluid propagation is from about 5 $\mu$J to about 500 $\mu$J at pulse discharge repletion rates from about 1 Hz to 1 kHz. More preferably, the discharge repletion rates range from about 10 Hz to 500 Hz. Still more preferably, the discharge repetition rates range from about 50 Hz to 100 Hz.

It should be appreciated that slight variations in the technique are intended to fall within the scope of the invention, such as introducing the electrolytic fluid and pharmacologic agent AG under pressure from 1 to 30 seconds before actuating the electrical discharge to thus develop thrombolytic effects in advance of the acoustic wave propagation.

Any sequence of such agent thrombolysis and electroacoustic waves are intended to fall within the scope of the inventive technique. While the invention is particularly adapted for small diameter circulatory arteries in the brain, it should be appreciated that the catheter may be used to dissolve thrombus in any part of the patient's circulatory system.

3. Type "B" Embodiment of Micro-Catheter

It should be appreciated that the thermal effect dissipation means and agent velocity dissipation means of present invention described above may be adapted for use with other energy delivery means, for example a laser source. The Type "B" embodiment would have a working end (not shown) that has all the similar dimensions as the Type "A"embodiment except that a laser source is provided to pump photonic energy along an optical fiber to recessed portion 25A. (see FIG. 1).

The photonic energy will then be absorbed by the introduced fluid EF which may be seeded with a suitable chromophore as is known in the art. Any suitable laser wavelength from about 100 nm to 3.0 μm may be used at repetition rates from 1 Hz to 50 kHz with energy densities from 0.1 to 5.0 J/cm2, with the preferred wavelength being in the infrared portion of the spectrum that is absorbed in water in the seed fluid.

4. Type "C" Embodiment of Micro-Catheter

The Type "C" embodiment would have a working end (not shown) that has all the similar dimensions as the Type "A" embodiment except that both an electrical discharge source and the Type "B" laser source would be provided to deliver thermal energy to the working end discharge zone DIZ within recessed portion 25A. (see FIG. 1).

The electrical discharge energy and photonic energy will then be absorbed by the introduced fluid EF which may be seeded and it is believed that such combination of electrical discharge and laser pulses, since delivering thermal effects by entirely different means, will allow very repetition rates, for example from 1 kHz to 100 kHz with very small energy densities from 0.1 to 1.0 J/cm2 which may prove to be useful parameters for some dissolving some thrombi.

Such use of combination electrical discharge and photonic energy was first disclosed by the inventor in the following United States patent applications: Ser. No. 09/049,711, filed Mar. 27, 1998 titled "Ionothermal Delivery System and Technique for Medical Procedures"; Serial No. 60/080,248, filed Apr. 1, 1998 titled "Ionothermal System and Technique for Refractive Procedures"; and Serial No. 60/080,244, filed Apr. 1, 1998 titled "Ionothermal System and Technique for Dermal Treatment".

It should be appreciated that slight variations in the technique are intended to fall within the scope of the invention, such as introducing the electrolytic fluid and pharmacologic agent AG under pressure from 1 to 30 seconds before actuating the electrical discharge to thus develop thrombolytic effects in advance of the acoustic wave propagation. Any sequence of such agent thrombolysis and electroacoustic waves are intended to fall within the scope of the inventive technique. While the invention is particularly adapted for small diameter circulatory arteries in the brain, it should be appreciated that the catheter may be used to dissolve thrombus in any part of the patient's circulatory system.

It should be appreciated that catheter wall 44 may be provided with a lumen or other means known in the art for over-the-wire introduction of the working end 10 when a guidewire is used. Although particular embodiments of the present invention have been described above in detail, it will be understood that this description is merely for purposes of illustration.

Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A method for applying energy to endovascular media, comprising the steps of:

(a) providing apparatus comprising an electrical discharge source and a catheter having a working surface with a longitudinal open-ended channel therein that carries first and second spaced apart interior electrodes, the first and second electrodes coupled to the electrical discharge source;

(b) introducing the working surface of the catheter to a position proximate the targeted media;

(c) introducing a fluid having a specified electrical resistivity to the channel, thereby defining an interface of the working surface and the targeted media; and (d) establishing an intense electrical field across the fluid between the first and second electrodes thereby vaporizing the fluid to cause delivery of energy across the interface to the targeted media.

2. The method of claim 1 wherein steps (c) and (d) are repeated at repetition rate ranging from 1 Hz to 1 kHz.

3. The method of claim 1 wherein the vaporization creates pressure gradients that project the fluid in high velocity flows from the working surface.

4. The method of claim 3 wherein the fluid carries a pharmacological agent that is projected into the targeted media.

5. The method of claim 3 wherein the projected fluid is elevated in temperature thereby delivering thermal energy to the targeted media.

6. The method of claim 3 wherein the projected fluid carries a pharmacological agent thereby delivering chemical energy to the targeted media.

7. The method of claim 3 wherein the pressure gradient delivers acoustic energy to the targeted media.

8. A medical instrument for application of energy to body structure of a patient, comprising:

an instrument having a proximal handle end and a working end for positioning proximate to a targeted body structure thereby defining an energy-delivery interface between the working end and the body structure;

at least one bore in the working end terminating in a media entrance port in a working end surface, a proximal portion of the at least one bore fluidly coupled to a remote fluid media inflow source; and a thermal energy emitter carried at an interior portion of the at least one bore for causing vaporization of fluid media within the at least one bore to thereby cause high pressure gradients within the at least one bore to project high velocity flows of fluid media artifacts across the energy-delivery interface into the body structure.

9. The instrument of claim 8 further comprising a remote energy source and controller that delivers energy in intervals for causing the high pressure gradients.

10. The instrument of claim 9 wherein the energy delivery intervals range from about 1 Hz to 1 kHz.

11. The instrument of claim 8 wherein thermal energy emitter comprises at least one electrode coupled to an electrical source.

12. The instrument of claim 8 wherein thermal energy emitter comprises the terminal end of a light channel coupled to a light source.

13. The instrument of claim 8 wherein the artifact comprises a pharmacological agent.

14. The instrument of claim 8 wherein the artifact comprises an electrically resistive or sensative composition.

15. The instrument of claim 8 wherein the artifact comprises a chromophore.

16. A medical instrument for application of energy to a surface of structure with a patient's body, comprising:

an instrument having a proximal handle end and a working end for positioning proximate to a targeted body structure thereby defining an energy-delivery interface between the working end and the body structure;

a channel in the working end fluidly coupled to a remote fluid media inflow source;

a thermal energy emitter carried at an interior portion of the channel coupled to a remote energy source; and an energy source and controller that delivers energy pulses to the emitter having a selected fluence, pulse duration and repetition rate that vaporizes fluid media proximate to the emitter thereby creating very high fluid pressures in the channel to cause high velocity projection of fluid media artifacts from the working end into the body structure.

17. The instrument of claim 16 wherein thermal energy emitter comprises at least one electrode coupled to an electrical source.

18. The instrument of claim 16 wherein thermal energy emitter comprises the terminal end of a light channel coupled to a light source.

19. The instrument of claim 18 wherein the light source emits a wavelength ranging between about 100 nanometers and 3.0 micrometers.

20. A method for applying energy to a targeted structure of a patient's body, comprising the steps of:

providing apparatus comprising a thermal energy emitter in the interior of an open-ended channel in an instrument working end surface, the emitter coupled to a remote energy source and controller;

introducing the working end surface of the apparatus to a position proximate the targeted structure;

introducing a fluid having a specified heat capacity into the open-ended channel, thereby defining an interface of the working end surface and the targeted structure; and delivering energy pulses having a selected fluence, duration and repetition rate to fluid media captured proximate to the emitter to vaporize the fluid thereby creating fluid pressures in the channel that project fluid media artifacts across the interface carried by high velocity fluid media flows from the working end surface.

21. The method of claim 20 further comprising delivering the energy pulses at a specified rate.

22. The method of claim 20 wherein the artifacts carried by the fluid media flows comprises a pharmacological agent.

23. The method of claim 20 wherein the high velocity fluid media flow is elevated in temperature thereby applying thermal energy to the targeted structure.

* * * * *